US007556035B2

(12) United States Patent
Young et al.

(10) Patent No.: US 7,556,035 B2
(45) Date of Patent: Jul. 7, 2009

(54) UNIT DOSE DRY POWDER INHALER

(75) Inventors: Matthew E. Young, Cambridge (GB); Stuart Brian William Kay, Cambridge (GB); Neil Richard Harrison, Birmingham (GB); Michael W. Ligotke, San Diego, CA (US)

(73) Assignee: Quadrant Technologies Limited, Ruddington, Nottingham (GB)

( * ) Notice: Subject to any disclaimer, the term of this patent is extended or adjusted under 35 U.S.C. 154(b) by 639 days.

(21) Appl. No.: 11/130,970

(22) Filed: May 17, 2005

(65) Prior Publication Data
US 2005/0284473 A1 Dec. 29, 2005

Related U.S. Application Data

(60) Provisional application No. 60/575,137, filed on May 28, 2004.

(51) Int. Cl.
*A61M 15/00* (2006.01)
(52) U.S. Cl. .............................. 128/203.15; 128/203.12; 128/203.23
(58) Field of Classification Search ............ 128/203.15, 128/203.19, 203.21, 203.12, 203.23, 200.22; 604/58
See application file for complete search history.

(56) References Cited

U.S. PATENT DOCUMENTS 5,829,434 A 11/1998 Ambrosio et al.
5,921,237 A * 7/1999 Eisele et al. ........... 128/203.21
6,427,688 B1 8/2002 Ligotke et al.
2002/0033177 A1 3/2002 Ohki et al.
2003/0015195 A1* 1/2003 Haaije de Boer et al. ..................... 128/203.15
2003/0188747 A1 10/2003 Ohki et al.

FOREIGN PATENT DOCUMENTS

GB 2064336 A 6/1981
WO WO 03/080149 A2 10/2003

OTHER PUBLICATIONS

Combined International Search Report and Written Opinion of the International Searching Authority for PCT/GB2005/002094 dated Aug. 17, 2005.

* cited by examiner

*Primary Examiner*—Steven O Douglas
(74) *Attorney, Agent, or Firm*—Kenneth H. Ohriner; Perkins Coie LLP

(57) ABSTRACT

A unit dose dry powder inhaler includes a chamber housing containing a powder dispersion chamber. A chamber tube extends from the dispersion chamber into the mouthpiece. A cover or cup is rotatably attached to the chamber housing. A dose of a dry powder is contained at a powder location in the chamber housing. An air passageway leading from the powder location to the dispersion chamber is closed off by the cover. When the cover is rotated to an open position, the air passageway is opened. The user inhales on the mouthpiece drawing air through the powder location, the air passageway, the dispersion chamber and the chamber tube, through the mouthpiece and into the users lungs. The unit dose of dry powder is stored directly in, or is part of, the inhaler.

11 Claims, 5 Drawing Sheets

UNIT DOSE DRY POWDER INHALER

Figure 1:
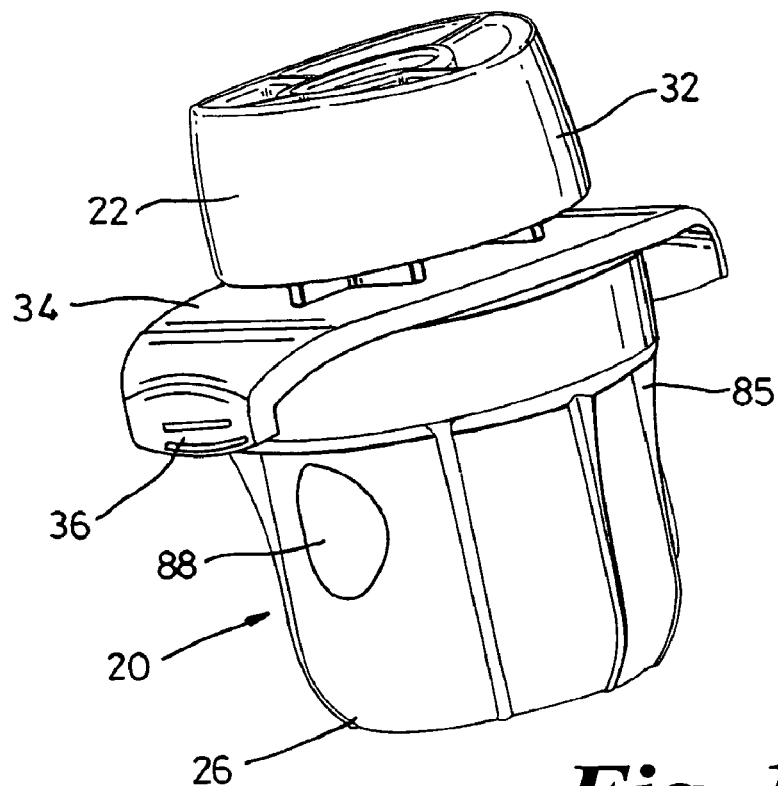

This application claims the benefit of U.S. Provisional Application No. 60/575,137 filed May 28, 2004.

BACKGROUND OF INVENTION

The field of the invention is dry powder inhalers.

Certain medicines may be inhaled in dry powder form directly into the lungs. Inhalation bypasses the digestive system and avoids any potential metabolic inactivation or destruction of the medicine by the digestive system. Inhalation can also provide very rapid onset of the effect of the medicine. Inhalation may also allow smaller doses to be used to achieve the same desired results as orally ingested medicines. In other cases, it provides a delivery technique for medicines that display unacceptable side effects when taken by other methods. In addition, inhalation also avoids the potential risks of injection to both medical caregivers and patients.

Various inhaler designs have been proposed, to allow dry powder medicines to be inhaled. Most of these inhalers are metered dose inhalers or multiple dose dry powder inhalers. Metered dose inhalers dispense a suspension of powder particles in a compressed propellant gas. Multiple dose dry powder inhalers generally repeatedly dispense individual doses from a bulk powder reservoir, or from a blister disk or cassette. However, certain medicines, such as certain peptides or proteins, or medicines such as vaccines, antidotes, etc., are generally taken by a patient infrequently or even only one time. Metered dose inhalers and multiple dose dry powder inhalers are not intended or well designed for one-time use, to deliver a single dose. These types of inhalers are typically too bulky, costly, inefficient, or difficult to use, when only a single dose is desired, and where the inhaler can be practically discarded after use, in an environmentally acceptable way.

Several unit dose inhalers, intended for one-time use, have been proposed. However, they have not achieved widespread use. Disadvantages remain with unit dose inhalers relating to powder storage, dose uniformity, dispersion performance, ease of use, cost, and other factors. Accordingly, there is a need for an improved inhaler for efficiently providing a single dose of a powdered drug.

It is an object of the invention to provide such an improved unit dose dry powder inhaler.

SUMMARY OF THE INVENTION

A unit dose dry powder inhaler has a chamber housing including a dispersion chamber. An air flow passageway extends through the chamber housing, and through the dispersion chamber. A dose of a dry powder pharmaceutical is contained at a powder location on or in the chamber housing. A cover or cup attached to the chamber housing is pivotable relative to the chamber housing from a first position, where the air flow passageway is closed off from the powder location, to a second position, where the air flow passageway connects through the powder location. The powder is stored directly within the inhaler itself. The powder can be quickly and easily inhaled by twisting or turning the cover, to open up the air flow passageway through the powder location.

In a second aspect, the dispersion chamber contains one or more beads, to improve dispersion of the powder.

In a third aspect, a ratchet or anti-reverse movement device is provided on the cover or the chamber housing, to help avoid inadvertent attempts to inhale a dose of powder from a used or empty inhaler.

Other and further aspects and advantages are also described. The invention resides as well in subcombinations of the components and method steps described and shown.

BRIEF DESCRIPTION OF THE DRAWINGS

In the drawings, wherein the same reference number indicates the same element, in each of the views:

FIG. 1 is a top and front perspective view of a unit dose dry powder inhaler.

FIG. 2 is a bottom and rear perspective view of the inhaler shown in FIG. 1.

FIG. 3 is a perspective view similar to FIG. 1, and with the cover or cup removed, for purpose of illustration, to show the chamber housing.

FIG. 4 is a perspective view similar to FIG. 2, and with the cover or cup removed, for purpose of illustration, to show the chamber housing.

FIG. 5 is a bottom perspective view of the top or mouthpiece section shown in FIGS. 1-4.

FIG. 6 is an inverted perspective view of the top section shown in FIG. 5.

FIG. 7 is a top perspective view of the base section shown in FIGS. 3 and 4.

FIG. 8 is a bottom perspective view of the base section shown in FIG. 8.

FIG. 9 is a top perspective view of the cover element shown in FIGS. 1 and 2.

FIG. 10 is plan view of the cover element shown in FIG. 9.

DETAILED DESCRIPTION OF THE DRAWINGS

Turning now in detail to the drawings, as shown in FIGS. 1-4, an inhaler 20 has a top or mouthpiece section 22 rigidly attached to a base 24, to form a chamber housing 100. A cup or cover 26 fits over and is pivotably attached to the chamber housing 100. The inhaler 20 is advantageously provided within a sealed pouch or container 28 as shown in FIG. 2. The inhaler 20 is preferably removed from the pouch immediately before use, to better reduce adverse environmental affects on the dose of powder.

The top section 22 includes a mouthpiece 32 extending out or up from a finger grip plate 34. Finger tabs 36 on the finger grip plate 34 provide convenient and secure finger positions for holding the inhaler 20. As shown in FIGS. 5 and 6, a first or top curved chamber wall 42 is formed in the underside of the mouthpiece section 22, opposite from the mouthpiece 32. A chamber tube 40 extends from a central area of the chamber wall to or through the mouthpiece 32. A top chamber inlet groove 46 extends outwardly at an angle from the chamber wall 42. A snap groove 52 is located along the lower edge of the top section 22. A top air inlet 38 passes through the lower lip of the snap groove 52. A raised chamber rim or shoulder 48 surrounds the chamber wall 42. Attachment holes 50 in the top section 22 are used to attach and align the base 24 onto the top section 22.

Referring now to FIGS. 7 and 8, the base 24 has a flange 64 extending radially outwardly from a cylinder section 65. A dose bowl or recess 74 is formed in the cylinder 65, and is surrounded by a bowl rim or raised shoulder 76. As shown in FIG. 3, a visual indicator 96, is provided on the outside of the cylinder, opposite or directly across from the dose bowl 74. A flange inlet 68 and a flange outlet 63 extend through the flange 64, on opposite sides of the dose bowl 74. Horizontal spacer ribs 94 project outwardly from the cylinder 65, opposite from the dose bowl 74, and extend across an arc of 60-270, 90-210 or 110-180 degrees. Ratchet teeth or recesses 71 and 73 are located about 90 degrees apart on or in the flange 64. A stop tooth is similarly located about 90 degrees apart from the tooth 73 on the flange 64. Attachment pegs 70 extend up or out from the flange 64 for engagement into the holes 50 in the top section 22. A curved second or bottom chamber wall 60 is formed in the base 24 and is surrounded by a raised bottom chamber rim 61. A bottom chamber inlet groove 62 extends from the flange outlet 63 to the bottom chamber wall 60.

As shown in FIGS. 3-8, the top or mouthpiece section 22 and the base 24 are joined together, with the pegs 70 in the holes 50. The top or first chamber wall 42 in the mouthpiece section 22 comes together with the second or bottom chamber wall 60 in the base 24 to form a dispersion chamber, generally indicated as 45 in FIG. 3. One or more beads 44 may optionally be contained within the dispersion chamber 45. The raised top chamber rim 48 around the top chamber wall 42 contacts with the raised bottom chamber rim 61 around the bottom chamber wall 60. The bottom chamber inlet groove 62 aligns with the top chamber inlet groove 46, to form a chamber inlet passageway 69 connecting the flange outlet 63 with the dispersion chamber 45. The top or first air inlet 38 in the mouthpiece section 22 is permanently fixed in position or aligned over the flange inlet 68 in the base. The mouthpiece section 22 and the base 24 may be joined via adhesives, welding, pressing, or with other known techniques. The beads 44, if used, are placed into the dispersion chamber 45 before the mouthpiece section and the base are permanently and irrotatably joined together. When joined together, the mouthpiece section 22, the base 24, and the bead or beads 44 (if used), form the chamber housing 100.

Figure 2:
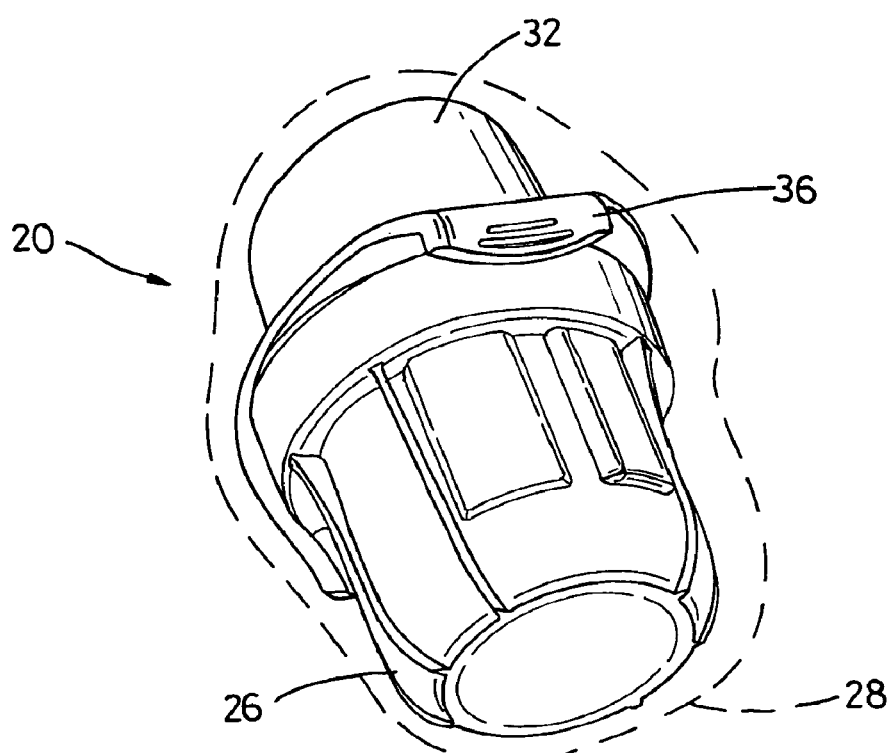
Figure 3:
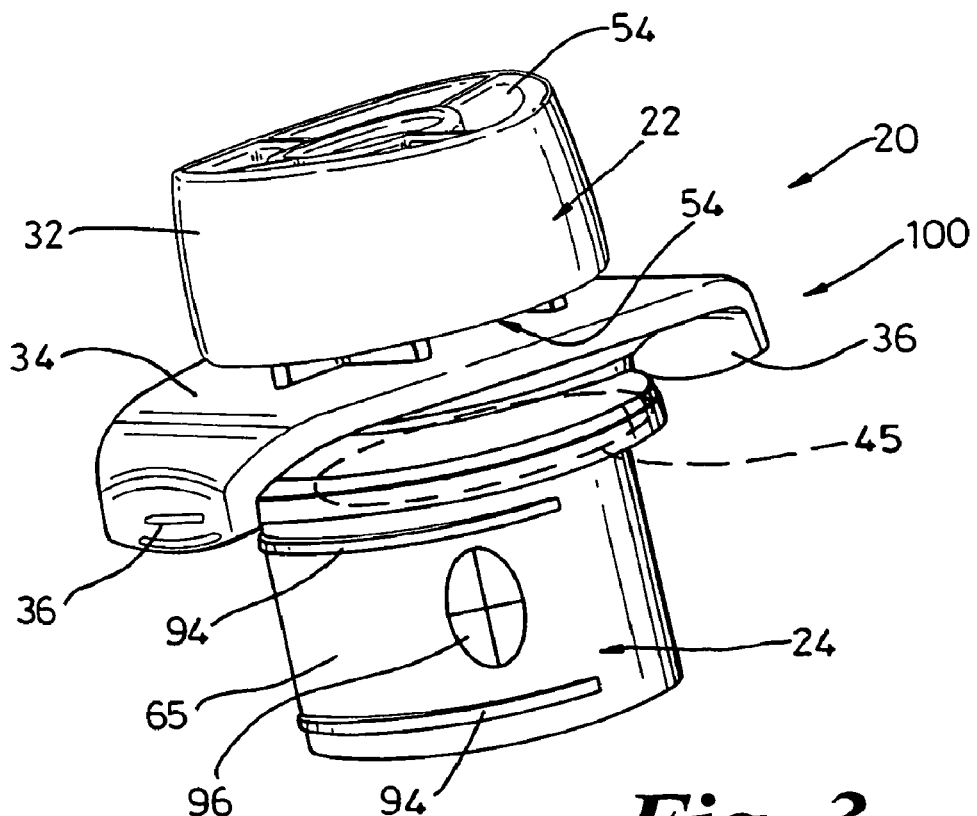
Figure 4:
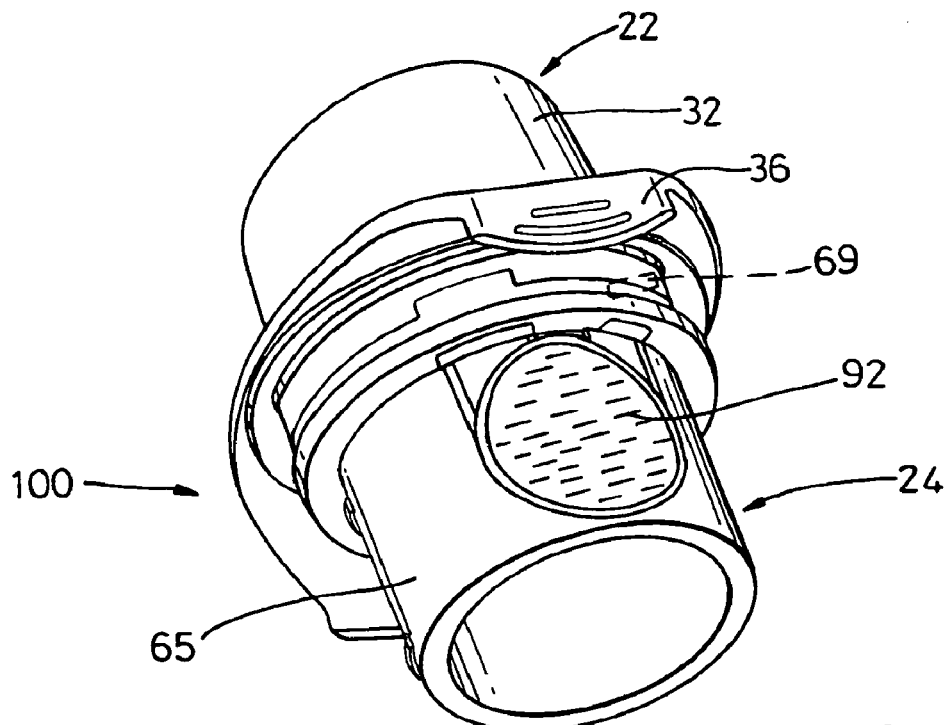
Figure 5:
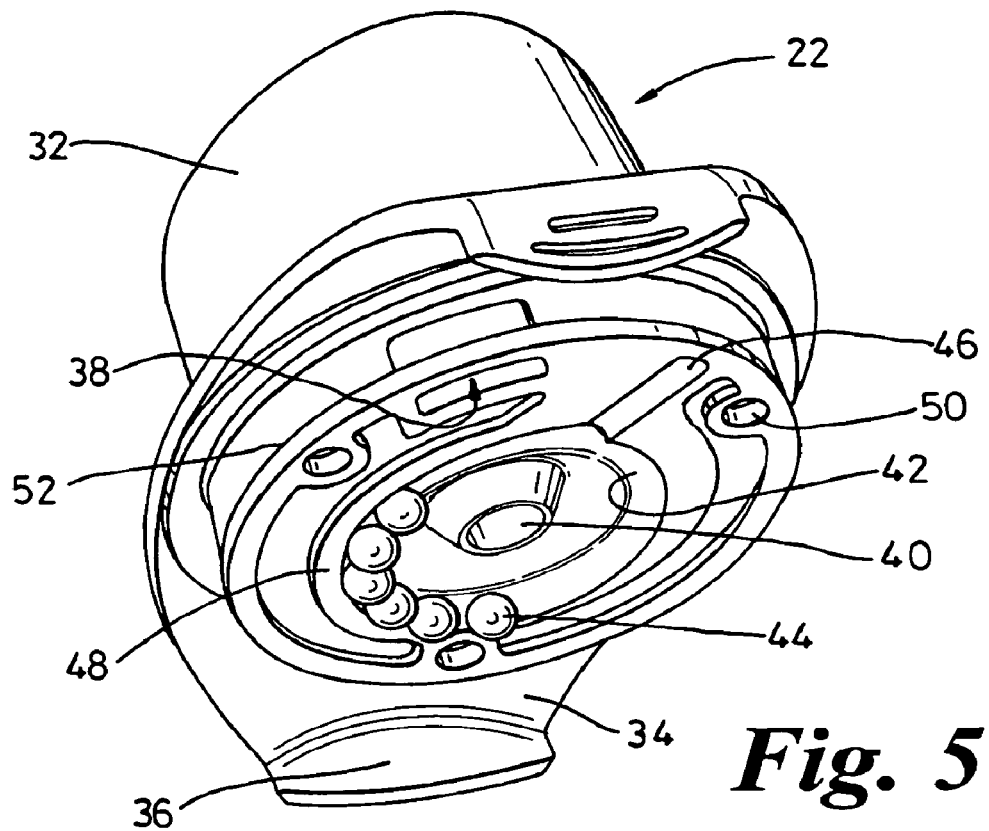
Figure 6:
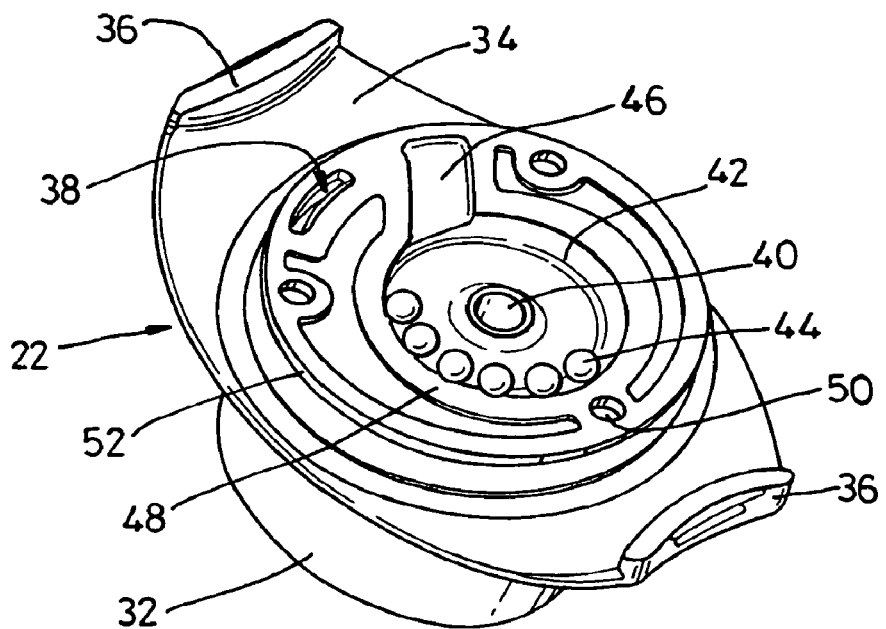
Figure 7:
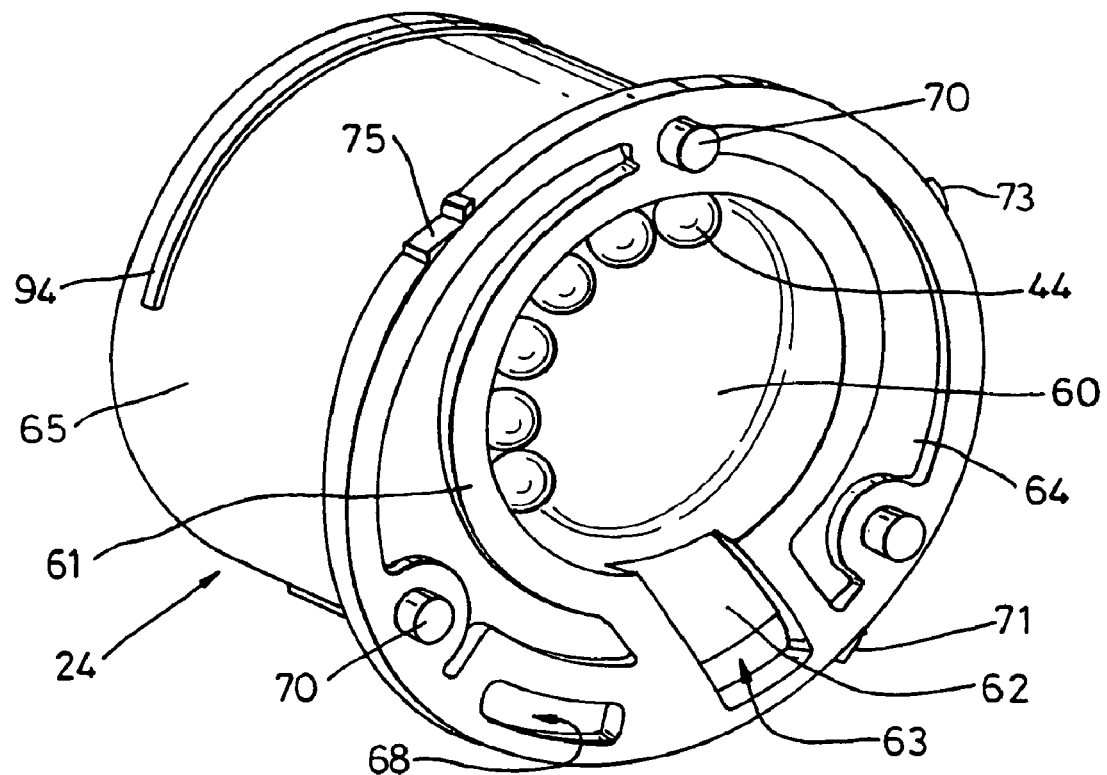
Figure 8:
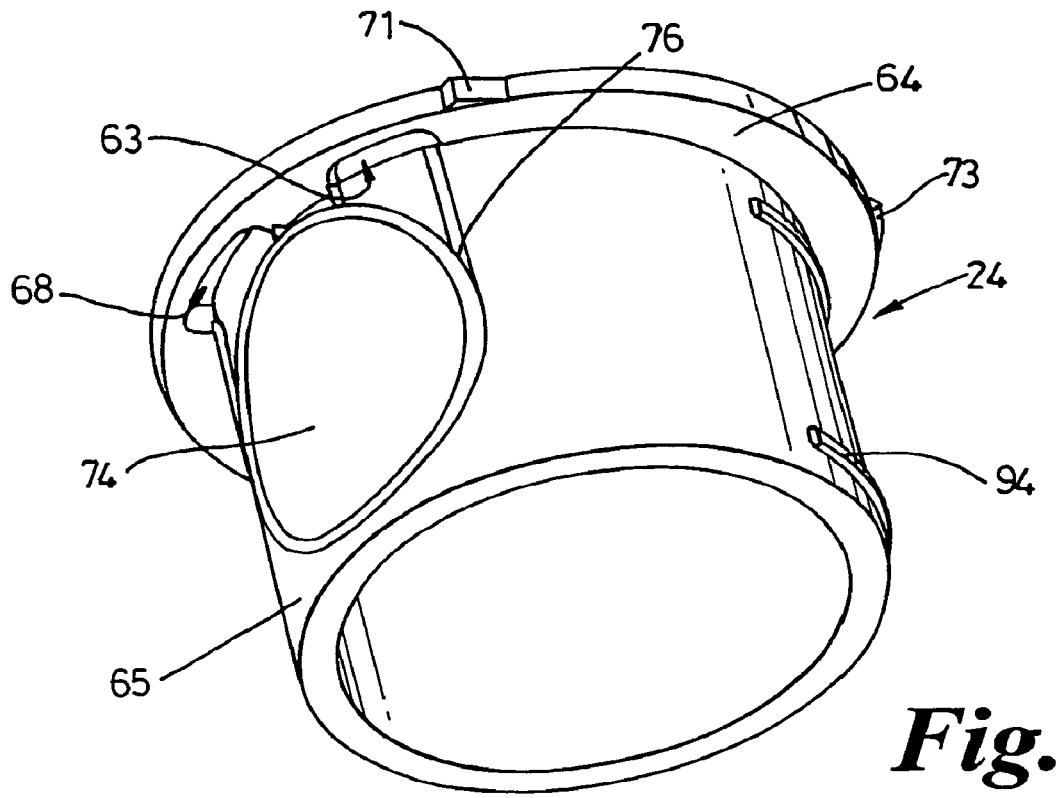
Figure 9:
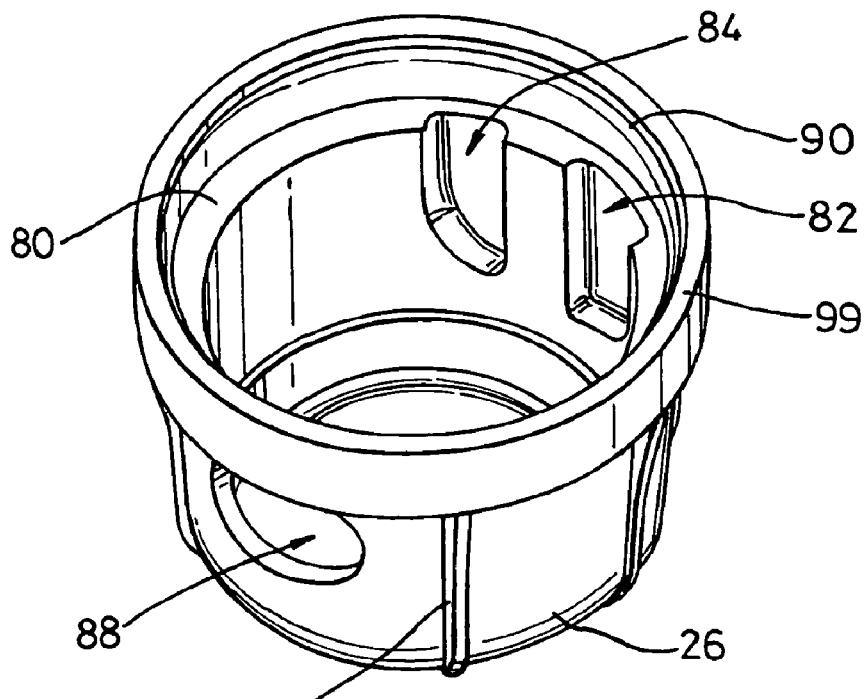
Figure 10:
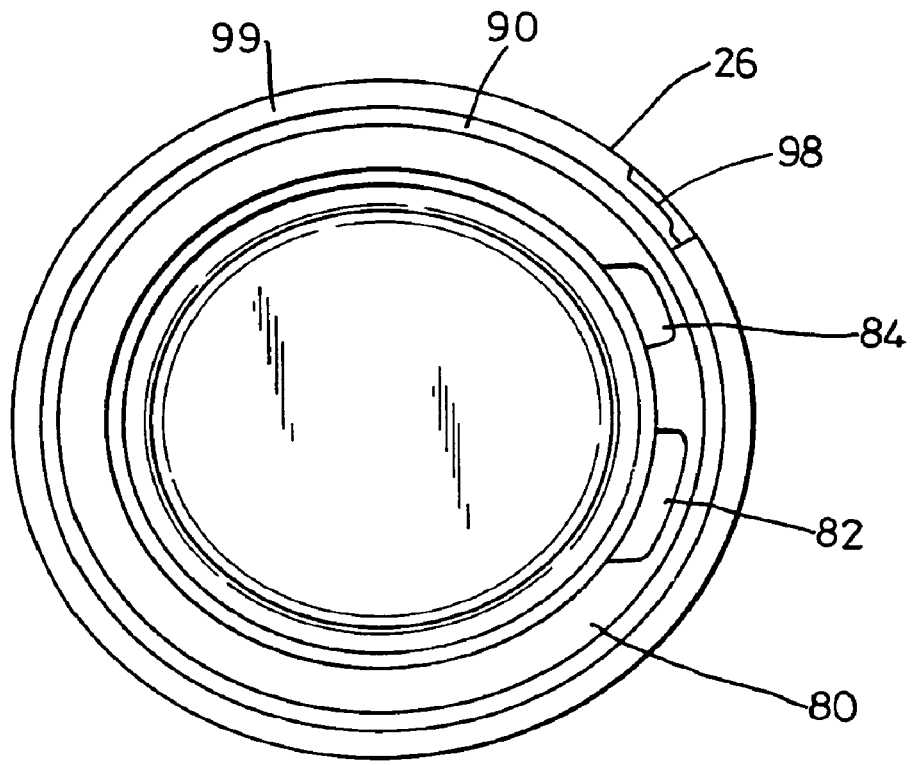

Turning to FIGS. 9 and 10, a snap ring projection 90 is formed on the inside diameter of a cover flange 80. A cover inlet slot 82 and a cover outlet slot 84 are formed in the cylindrical sidewall of the cover. The slots 82 and 84 are located on the cover and dimensioned so that they can be aligned respectively with the flange outlet 63 and the flange inlet 68 in the flange 64 of the base 24. One or more ribs 85 are preferably provided on the outside cylindrical walls of the cover 26. A ratchet arm 98 is formed on the lip 99 of the cover 26. A dose loading hole 88 is provided in the cylindrical sidewall of the cover, opposite from the slots 82 and 84. As shown in FIG. 2, the bottom of the cover 26 is flat or has a central concave area, to allow the inhaler 20 to stand upright on a flat surface.

Referring to FIGS. 3, 4, 9 and 10, the cover 26 is attached to the mouthpiece section 22 via the snap ring 90 snapping into the groove 52. The inhaler 20 is then assembled, as shown in FIGS. 1 and 2, and is ready for loading with a single dose 92 of a dry powder pharmaceutical.

The mouthpiece section 22, the base 24 and the cover 26 are preferably molded of a plastic material, allowing them to be manufactured inexpensively, using a minimum amount of material. Molding also allows for convenient formation of various of the features described above. However, various other manufacturing techniques, involving forming the mouthpiece section, base and cover as integral components, or involving making them via assembly of discrete sub-components, may of course also be used.

With the inhaler 20 initially assembled, the dose loading hole 88 is aligned over the dose bowl 74, and the inhaler 20 is laying on its side, with the dose bowl facing up. A dose of a dry powder pharmaceutical powder 92 is placed into the bowl, through the hole 88, preferably using an automated powder loading system. The cover 26 is then turned or rotated by about 90 degrees. This moves the bowl 74 containing the powder 92 to a midpoint between the loading hole 88 and the slots 82 and 84. The inhaler 20 is thus in the storage position, and may be sealed into the pouch or package 28 and sealed. In the storage position, the flange inlet 68 and the flange outlet 63 to the bowl 74 are closed off by the cover flange 80.

The smooth cylindrical inside surface of the bowl 74 slides over the bowl rim 76. The bowl rim 76 helps to contain the powder within the bowl. The spacer ribs 94 space the inside cylindrical walls of the cover apart from the outside cylindrical walls of the cylinder 65 on the base 24. Consequently, the bowl makes sliding contact only with the bowl rim 76 and the spacer ribs 94. The bowl therefore remains aligned on the cylinder 65, and rotates only when a desired amount of turning force or torque is applied. This prevents inadvertent turning of the bowl during packaging, shipment and handling. However, it also allows the bowl to turn when nominal force is applied, so that users with low hand and finger strength or dexterity are able to use the inhaler.

In use, the inhaler 20 is removed from the package 28. The user grasps the finger tabs 36 with one hand and rotates the cover by about ¼ turn or 90 degrees, to an open position. The ratchet arm 98 allows the cover to be rotated only in the forward direction (counterclockwise in FIG. 2). The ratchet arm may also provide an audible and/or tactile click or pop when the open position is reached. A detent or an open position stop pin or boss may also be provided, to help insure that the cover is correctly and fully moved into the open position. The visual indicator 96 is aligned in the dose loading opening 88, providing a visual indication to the user that the inhaler is in the open or ready to use position.

The pivoting movement of the cover 26 opens the air flow passageways in the inhaler 20. A first air flow path is formed via the top or first inlet 38 and the flange inlet 68, which are permanently open. A second air flow path is formed by the flange outlet 63, the chamber inlet 69, the dispersion chamber 45, and the chamber tube 40. With the inhaler in the storage position, the first airflow path is closed off from the second air flow path by the lip 99 of the cover 26, as the slots 80 and 82 are not aligned with the openings 63 and 68 in the flange 64. When the cover 26 is turned further into the open or ready position, as described below, the first and second air flow paths are connected through the bowl 74 and the slots 82 and 84 in the sidewall of the cover 26.

In the open position, the flange inlet 68 and outlet 63 to the bowl 74 are now open, as they are aligned with the slots 82 and 84 in the cover 26 Thus, in the open position, there is an unobstructed continuous air flow path through the inhaler. The user inhales on the mouthpiece 32. Air flows in the top inlet 38, through the flange outlet 63, into the cover inlet slot 82, through the bowl 74, and then out of the bowl through the cover outlet slot 84, the flange inlet 68, and into the dispersion chamber 45 via the chamber inlet passageway 69. As air flows through or over the bowl 92, powder is entrained in the air. The inlet and outlet slots 82 and 84 connect tangentially into the bowl 74. This provides a swirling air movement, to enhance entrainment of the powder into the flowing air.

The air/powder mixture flows into the dispersion chamber, where the powder is more effectively dispersed, to provide better inhalation performance. Dispersion in the chamber 45 occurs via rapid circular movement of the powder and air. In embodiments containing beads in the chamber, the beads assist in dispersion, as described in U.S. Pat. No. 6,427,688 and U.S. Published Patent Application No. 2001/0027790A1, both incorporated herein by reference.

Air and dispersed powder flow out of the dispersion chamber 45 through the chamber tube 40 and mouthpiece 32, and are inhaled by the user. Sheath air channels 54 may be provided around the chamber tube, to surround the powder-laden stream of inhaled air with ambient air. Use of sheath air reduces deposition of powder in the mouth and throat, so that more of the powder is delivered into the lungs of the user.

After use, the cover 26 is optionally rotated an additional ¼ turn, into a used or discard position. The stop boss or pin 75 engages with the ratchet arm 98, to prevent the cover from turning in either direction. Accordingly, in the used position, the cover is locked and cannot turn, and the visual indicator 96 is not visible. This indicates to the user that the inhaler is used and should be discarded. Hence, turning the cover into the used position helps to prevent attempts to inhale a dose from a used inhaler.

The specific size, shape and arrangement of various of the features shown FIGS. 1 and 2, including the finger plate 34 and tabs 36, mouthpiece 32, ribs 85, and the cover 26, is arbitrary. The appearance of these features is a matter of design preference from a large array of options. These features may be selected or changed to create any desired ornamental external appearance of the inhaler 20.

Thus, a novel unit dose dry powder inhaler has been shown and described. Many changes, substitutions and uses of equivalents may of course be made without departing from the spirit and scope of the invention. The invention, therefore, should not be limited, except by the following claims and their equivalents.

The invention claimed is:

1. A unit dose dry powder inhaler, comprising:
- a chamber housing;
- a cover rotatably attached to the chamber housing;
- a dispersion chamber in the chamber housing;
- a powder storage location in or on the housing;
- a dose of a dry powder pharmaceutical powder at the powder storage location enclosed by the chamber housing and the cover;
- an air flow passageway extending at least from the powder storage location through the dispersion chamber and to the mouthpiece; and
- opening means for opening or closing off the air flow passageway by rotating the cover relative to the chamber housing.

2. A unit dose dry powder inhaler, comprising:
- a mouthpiece section having a mouthpiece, a first chamber wall, and a chamber tube extending from the top chamber wall through the mouthpiece;
- a base joined to the mouthpiece section and having a second chamber wall, with the first and second chamber walls forming a powder dispersion chamber;
- a chamber air inlet in one or both of the mouthpiece section and the base, with the air inlet extending into the dispersion chamber;
- a cover rotatably attached to the mouthpiece section or the base, with the cover and the base containing a dose of a dry powder pharmaceutical between them; and
- an air passageway which can be closed off from or aligned with the chamber air inlet by pivoting the cover relative to the base.

3. A unit dose dry powder inhaler comprising:
- a chamber housing including a dispersion chamber and a first air flow passageway connecting into the dispersion chamber; and
- a cup pivotably attached to the chamber housing and the chamber housing and the cup forming a second air flow passageway between them leading through a powder storage location, and with the cup pivotable relative to the chamber housing from a first position, wherein the second air flow passageway is closed off from the first air flow passageway, to a second position, wherein the second air flow passageway is substantially connecting into the first air flow passageway, to allow for air flow through the chamber housing and the cup, and through the dispersion chamber.

4. The unit dose dry powder inhaler of claim 3 further comprising a dose loading hole in a side wall of the cup substantially opposite from the second air flow passageway, and with the cup pivotable relative to the chamber housing into a third position, wherein the dose loading hole is substantially aligned with the powder storage location.

5. A unit dose dry powder inhaler comprising:
- a top joined to a base to form a chamber housing containing a first air flow path leading through a dispersion chamber;
- a second air flow path leading through an inlet and an outlet and through a powder storage chamber, in the base;
- a cover pivotably attached to the chamber housing;
- with the cover pivotable relative to the chamber housing from a first position, wherein the second air flow path is substantially closed off from the first air flow path by a flange on the cover closing off the inlet and outlet, to a second position, wherein the second air flow path is substantially connected to the first air flow path by opening up the inlet and outlet slots, to allow for air flow through the second and first parts, and through the dispersion chamber.

6. The unit dose dry powder inhaler of claim 5 with the powder storage compartment formed in a substantially cylindrical sidewall of the base and covered by a substantially cylindrical sidewall of cover.

7. The unit dose dry powder inhaler of claim 5 with the second air flow path leading into the powder compartment in a first direction and leading out of the powder compartment in a second direction generally opposite from the first direction.

8. The unit dose dry powder inhaler of claim 5 wherein the first part includes a top section joined to a base section to form a chamber housing containing the dispersion chamber.

9. The unit dose dry powder inhaler of claim 8 wherein the second part comprises a cover pivotably attached to the chamber housing and with the cover having inlet and outlet slots alignable to connect the first and second air flow paths through the powder compartment.

10. The unit dose dry powder inhaler of claim 9 with the base section including a base flange having an inlet opening and an outlet opening extending through the flange and alignable respectively with the inlet and outlet slots in the cover, when the second part is in the second position.

11. The unit dose dry powder inhaler of claim 9 further including a ratchet device on at least one of the cover and the base section, to allow the cover to rotate in only one direction.

* * * * *